United States Patent
Endres et al.

(10) Patent No.: US 12,019,002 B2
(45) Date of Patent: Jun. 25, 2024

(54) READY-TO-EXTRACT PLATFORMS FOR CHEMICAL ANALYSIS AND QUANTIFICATION OF UNKNOWN SAMPLES USING SPIKED MATRIX STANDARDS

(71) Applicant: PinPoint Testing, LLC, Little Rock, AR (US)

(72) Inventors: Gregory William Endres, Saline, MI (US); Jeffery H. Moran, Roland, AR (US)

(73) Assignee: PinPoint Testing, LLC, Little Rock, AR (US)

( * ) Notice: Subject to any disclaimer, the term of this patent is extended or adjusted under 35 U.S.C. 154(b) by 689 days.

(21) Appl. No.: 16/919,927

(22) Filed: Jul. 2, 2020

(65) Prior Publication Data

US 2021/0003488 A1    Jan. 7, 2021

Related U.S. Application Data

(60) Provisional application No. 62/870,436, filed on Jul. 3, 2019.

(51) Int. Cl.
  *G01N 1/40*    (2006.01)
  *G01N 33/03*   (2006.01)

(52) U.S. Cl.
  CPC .......... *G01N 1/4055* (2013.01); *G01N 33/03* (2013.01); *G01N 2001/4061* (2013.01)

(58) Field of Classification Search
  None
  See application file for complete search history.

(56) References Cited

U.S. PATENT DOCUMENTS

| | | | |
|---|---|---|---|
| 8,410,064 B2* | 4/2013 | Radominska-Pandya | C07H 17/04 514/23 |
| 10,502,750 B2* | 12/2019 | Giese | B01D 53/025 |
| 2009/0017555 A1* | 1/2009 | Jehanli | G01N 33/526 436/501 |
| 2016/0282371 A1* | 9/2016 | Huang | G01N 33/948 |
| 2017/0189902 A1* | 7/2017 | Moran | B01L 3/5085 |

* cited by examiner

*Primary Examiner* — Daniel S Larkin
(74) *Attorney, Agent, or Firm* — Honigman LLP; Fernando Alberdi

(57) ABSTRACT

The present disclosure provides a set of spiked matrix standards comprising: one or more carriers, each carrier comprising: (a) a reference standard analyte in an amount that is different in each carrier; and (b) a blank matrix that is in admixture or in contact with the reference standard analyte. Methods for preparing and quantitating an analyte in a test sample comprises (a) providing one or more test samples to be tested for the presence of the analyte (b) providing a set of spiked matrix standards; (c) processing the standards and test samples and (d) quantitating the amount of analyte in each of the standards and test samples.

6 Claims, 6 Drawing Sheets

READY-TO-EXTRACT PLATFORMS FOR CHEMICAL ANALYSIS AND QUANTIFICATION OF UNKNOWN SAMPLES USING SPIKED MATRIX STANDARDS

CROSS REFERENCE TO RELATED APPLICATIONS

The present application is a United States Non-Provisional Application under 35 U.S.C. § 111(a) claiming the benefit of, and priority to U.S. Provisional Patent Application Ser. No. 62/870,436, filed on Jul. 3, 2019, the disclosure of which is incorporated by reference herein in its entirety.

FIELD

The present invention relates to devices, kits, and methods for the quantitative analysis of a small molecule analyte or analytes in a sample.

BACKGROUND

Quantitative analysis of the components in a solid sample (i.e. plant material) or within a specific formulation (i.e. baked goods, gelatin products, oils, pills) requires different methods of sample extraction prior to analysis using a variety of analytical techniques. Quantitative assays known in the field require preparation of standard solutions within a given range of concentration, often and with the incorporation of internal standards at a fixed concentration. Such assays will also incorporate the use of second source quality control solutions and blank solutions that lack the analytes of interest. Ideally, a matrix blank or a representative matrix blank is utilized that contains all sample components except the analytes of interest and are subject to all sample processing steps. The role of the matrix blank is to measure the presence of interference from the matrix, known as the matrix effect. The high incidence of matrix effects in liquid chromatographic tandem mass spectrometric (LC-MS/MS) methods has led to several approaches that have been investigated to improve reproducibility and robustness of LC-MS/MS methods that are subjected to matrix effect. For example, Smeraglia et. al. (Chromatographia, January 2002, vol 55, suppl 1, pp S95-S99) describe an overview of methodological issues and techniques to improve the robustness of complex bioanalytical methods to avoid matrix-related issues. It is common practice to use a matrix blank that is similar in constitution to the sample matrix subjected to chemical analyses.

Quantitative assays that require the preparation of solutions from individual chemical components to be analyzed, as well as the use of blank matrix are time consuming and difficult to produce because of the high potential for human error. Common errors include liquid transfer mistakes when aliquoting a solution using a robotic liquid handler or hand-pipette to an incorrect tube or well-plate position, the transfer of the wrong amount of liquid, the transfer of an incorrect analyte, omission of a required analyte, and calculations errors of the solution concentrations. Assays that are designed for the simultaneous quantitation of multiple analytes often require hundreds of liquid transfers to produce the required solutions which results in ample opportunity for human error. Despite the critical importance of accurately prepared calibration solutions and the use of blank matrices, no product currently exists in a ready to use format that incorporates both. Furthermore, use of a blank matrix material in a quantitative assay without subjecting to all sample processing steps is not adequate, since any bias that is introduced as a result of the processing steps is disregarded. Thus, there is a need for matrix-specific methods and devices that are accurate, relevant, reliable, cost-effective, and easy to use while reducing human error.

The present disclosure addresses these issues by providing such a device as a high and medium throughput multi-component quantitative assay or test kit in a ready-to-extract format, with the precision and accuracy to meet the growing demand within several industries including but not limited to forensic, clinical, toxicology, research, environmental, food, and hemp/*cannabis*.

SUMMARY

The present disclosure provides devices or kits for quantifying the concentration of one or more analytes in a test sample. The device contains spiked matrix components and extraction solutions (ES). The ES may also be formulated to contain internal standards (IS). Exemplary analytes in this invention includes substances that may be classified as phytocannabinoids, terpenes, pesticides, heavy metals, and synthetic drugs. The spiked matrix components contain precise quantities of the analytes to be tested, imbedded within or on the matrix.

The present disclosure also provides a device or kit for quantitative determination of the concentration of one or more analytes, defined for the purpose of this disclosure, as up to 500 or more, for quantifying the concentration of one or any number of test samples.

The present disclosure also provides methods for determining the concentration of one or more analytes in any number of test samples using a device of the present disclosure, comprising the steps of: i) providing a device of the present invention wherein the device comprises a plurality of spiked matrix calibration standards with a range of analyte concentrations, spiked matrix quality control standards with a range of analyte concentrations, and blank matrix standards devoid of the analytes to be quantified; ii) optionally providing at least one extraction solution (ES) for each spiked matrix calibration standard and test sample; iii) optionally combining each spiked matrix calibration standard, each spiked matrix quality control standard, each blank matrix, and each sample for analysis to a separate ES vessel; iv) mixing the spiked matrix standards, blank matrix, and samples within the ES; v) filtering, centrifuging, or other preparative work to the ES vessel mixtures before analysis; and vi) quantifying the concentrations of the analytes present in the spiked matrix calibration standards, spiked matrix quality control standards, and the test samples.

In another related aspect, the present disclosure provides a device or kit operable to quantitatively and/or qualitatively measure the presence and/or amount of an analyte present in a test sample comprising the steps of: i) providing a device of the present invention wherein the device comprises a plurality of spiked matrix calibration standards with a range of analyte concentrations, spiked matrix quality control standards with a range of analyte concentrations, and blank matrix standards devoid of the analytes to be quantified; ii) adding at least one extraction solution (ES) for each spiked matrix calibration standard and test sample; iii) mixing or reconstituting the spiked matrix standards, blank matrix, and test samples with the ES; iv) optionally, separating any solids from the liquid component in the mixtures before analysis to obtain one or more clarified standard solutions and one or more clarified test solutions; and v) quantifying the concentrations of the analytes present in the matrix calibration standards, spiked matrix quality control standards and test samples, for example, the clarified spiked matrix calibration standards, clarified spiked matrix quality control standards, and the clarified test samples.

DETAILED DESCRIPTION

Definitions

Figure 1:
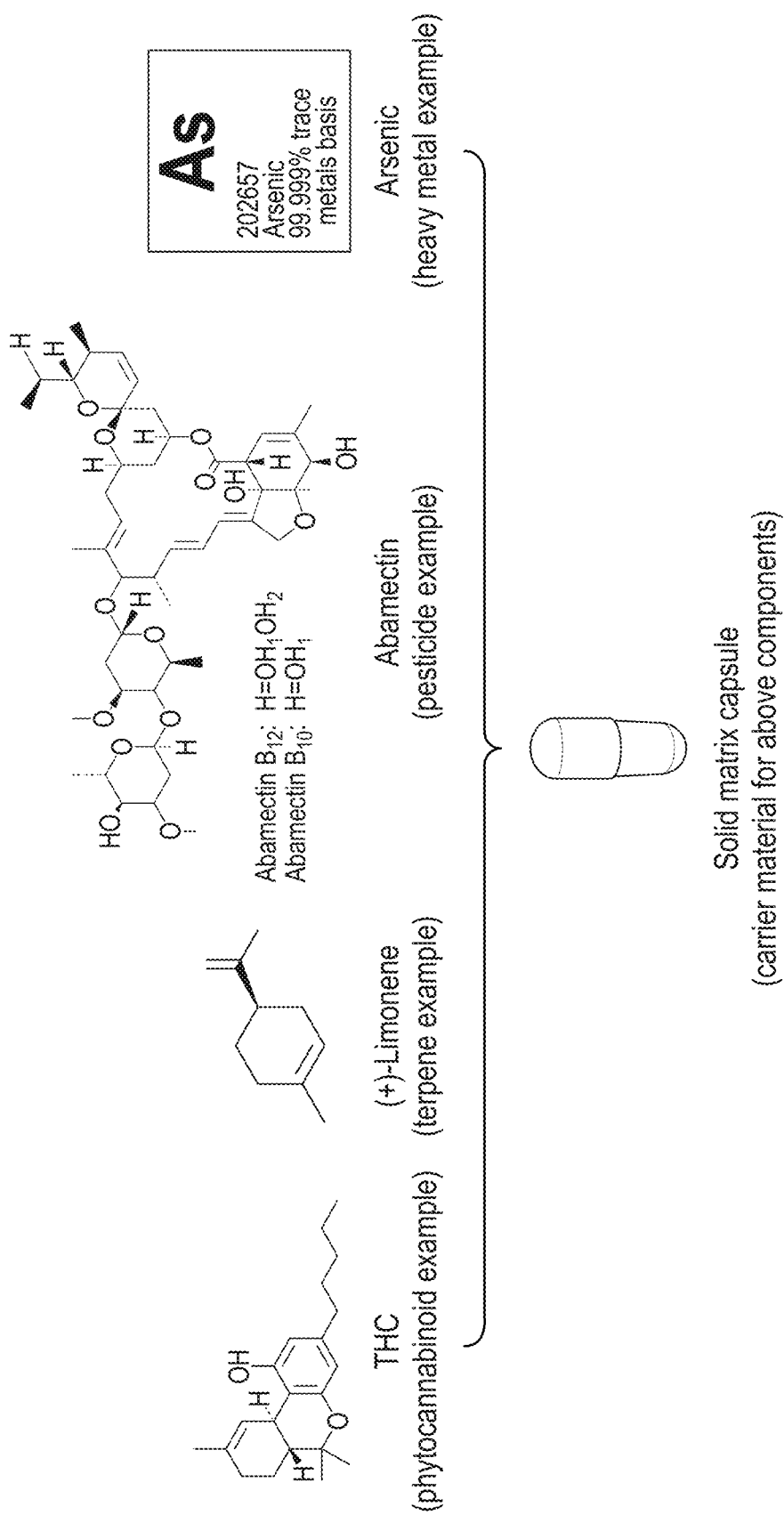
FIG. 1 illustrates an exemplary spiked matrix component in the form of a blank matrix capsule that contains one or more exemplary phytocannabinoid, terpene, pesticide and heavy metal examples, such as delta-9-THC, (+)-limonene, abamectin, and arsenic.
Figure 2:
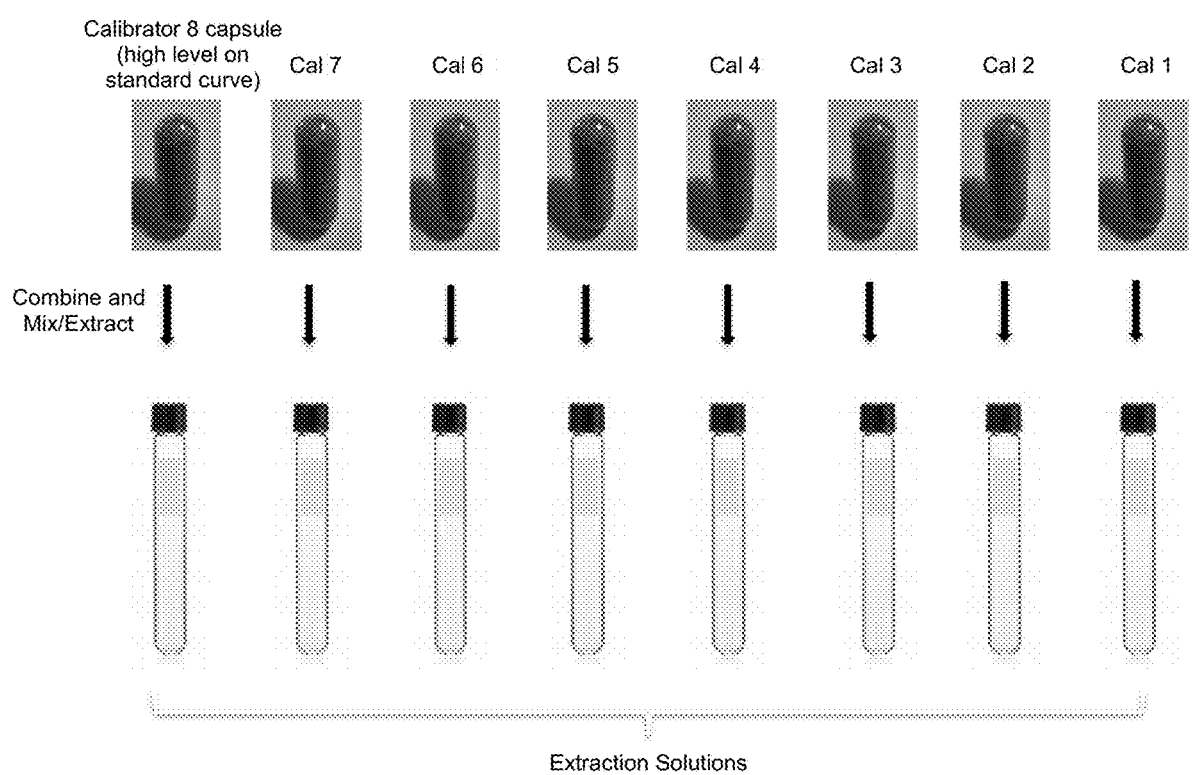
FIG. 2 depicts a set of eight spiked matrix calibrator standards and the workflow step and addition to the extraction solution vessels for mixing/extraction.

An "analyte" is defined as any element or small molecule with a molecular weight that is less than 1000 amu.

A "reference standard," or "standard" is used interchangeably within, and refer to a standardized analyte which is used as a measurement base for the analyte to be tested.

An "internal standard" and "IS" are used interchangeably herein and refer to a reference standard that is modified for detection or is a surrogate reference standard for detection. For example, the internal standard may be a reference standard having at least one atomic substitution in its molecular structure.

A "surrogate internal standard" (SIS) is a substitute for an internal standard. For example, the racemic (+/−)-delta-9-THC-d3 may be used as a surrogate for (−)-delta-9-THC-d3. Another example is the use of a non-isotopically labelled substance, such as (±)-11-nor-9-carboxy-$\Delta^9$-Tetrahydrocannabinol, as a surrogate for THCA-A.

A "calibration standard" and "Cal standard" are used interchangeably herein and refer to a reference standard that is used to calibrate an instrument reading with an amount of an analyte.

"Second-source quality control standard", "quality control standard" and "QC" are used interchangeably herein, and refer to a reference standard that is 1) obtained or prepared from a source independent of the source of the calibration standard, or 2) is obtained or prepared from a reference standard from the same source as the calibration standard but from a different lot than the reference standard used to prepare the calibration standard, or 3) the quality control standard is made from the same source and lot but from independent preparation. The second source quality control standard is used to verify the correctness of a calibration obtained using the calibration standard.

"Blank matrix" or "Matrix blank" is defined as a substance that is of the same material or similar material to the sample substance of associated test samples that is devoid of the analytes of interest. The matrix blank is also subject to all sample processing steps.

"Spiked Matrix" is defined as a substance that is of the same material or similar material to the sample substance of associated test samples that is manufactured to contain the analytes of interest. The spiked matrices are optionally subject to all sample processing steps.

"Spiked Matrix Calibration Standard" or "Spiked Matrix Calibrator" or "Spiked Matrix Cal" is defined as a substance that is of the same material or similar material to the sample substance of associated test samples that is manufactured to contain the analytes of interest at a specific concentration for use in a standard curve for calibration purposes. The spiked matrix Cal is also optionally subject to all sample processing steps.

"Spiked Matrix Quality Control Standard" or "Spiked Matrix QC" is defined as a substance that is of the same material or similar material to the sample substance of associated test samples that is manufactured to contain the analytes of interest at a specific concentration for use in quality control purposes. The spiked matrix QC is also optionally subject to all sample processing steps.

"Spiked Matrix Standard" is defined as a substance that is of the same material or similar material to the sample substance of associated test samples that is manufactured to contain the analytes of interest at a specific concentration for use in calibration or quality control purposes. The "spiked matrix calibration standard" and the "spiked matrix quality control standard" are both referred to as "spiked matrix standards". The spiked matrix standard is also optionally subject to all sample processing steps.

As used herein, the term "neat residue" refers to analytes, internal standards, or internal standard surrogates in the form of a solid or oil after removal of solvent.

"Matrix carrier" is defined as the vehicle to deliver the matrix and/or spiked matrix to the ES. An empty gelatin capsule would be an example of a matrix carrier that is used to deliver spike matrix to an ES. In another illustrative embodiment, avial is another example of a matrix carrier that may be used as a vessel for reconstitution of the matrix and/or spiked matrix with the ES.

Extraction solution (ES) is defined as a solution that is suitable for extraction of the type of matrix to be tested. The ES may also be a solution that contains internal standard(s) or surrogate internal standard(s) of the analytes to be tested.

QUECHER tube is defined as vessel that is used for solid phase extraction methods, eg SampliQ QuEChERS extract tubes (Agilent Technologies, item 5982-5550).

THC is an abbreviation for Delta-9-Tetrahydrocannabinol or Delta-8-Tertahydrocannabidiol.

CBD is an abbreviation for Cannabidiol.

CBN is an abbreviation for Cannabinol.

CBG is an abbreviation for Cannabigerol.

CBDA is an abbreviation for Cannabidiolic Acid.

CBDV is an abbreviation for Cannabidivarin.

CBC is an abbreviation for Cannabichromene.

CBT is an abbreviation for Cannabicitran.

CBV is an abbreviation for Cannabivarin.

CBCO is an abbreviation for Cannabichromeorcin.

THCA is an abbreviation for $\Delta$9-Tetrahydrocannabinolic Acid A.

CBDA is an abbreviation for Cannabidiolic Acid.

THCV is an abbreviation for Tetrahydrocannabivarin.

CBDV is an abbreviation for Cannabidivarin.

CBND is an abbreviation for Cannabinodiol.

CBE is an abbreviation for Cannabielsoin.

CBL is an abbreviation for Cannabicyclol.
CBCV is an abbreviation for Cannabichromevarin.
CBGV is an abbreviation for Cannabigerovarin.
CBGM is an abbreviation for Cannabigerol monomethyl ether.

"A", "an", "the", "at least one", and "one or more" are used interchangeable to indicate that at least one of the items is present; a plurality of such items may be present unless the context clearly indicates otherwise.

It is noted in this disclosure, terms such as "comprises", "comprised", "comprising". "contains", "containing", and the like have the meaning attributed in United States patent law; they are inclusive or open-ended and do not exclude additional, un-recited elements or method steps unless clearly specified otherwise in the present invention. Term such as 'consisting essentially of' and "consists essentially of' have the meaning attributed in United States Patent law; they allow for the inclusion of additional ingredients or steps that do not affect the basic or novel characteristics of the claimed invention. The terms "consists of", and "consisting of" have the meaning ascribed to them in United States Patent law; namely that these terms are close ended.

The antecedent "about" indicated that the values are approximate. For example, the range of "about 1 mg to about 50 mg" indicates that the values are approximate values. The range of "about 1 mg to about 50 mg" includes approximate and specific values, e.g., the range includes about 1 mg, and about 50 mg.

When a range is described, the range includes both the endpoints of the range as well as all numbers in between. For example, "between 1 mg to 10 mg" includes 1 mg, 10 mg and all amounts between 1 mg and 10 mg.

The present disclosure provides ready-to-use assay kits and methods for the rapid multiplex quantitative analysis of analytes in a test sample while eliminating the need for the end user to prepare standardized solutions of the analytes, calibration standards, second source quality control standards, or internal standards.

Devices

One aspect of the present invention provides an test kit or assay kit that comprises a set (one or more spiked matrix calibration standards and/or spiked matrix quality control standards) or sets of spiked matrix calibration standards and/or spiked matrix quality control standards wherein each spiked matrix standard is independently manufactured to contain a precise, pre-determined quantity of a calibration standard, and/or a precise, pre-determined quantity of a quality control standard, and/or blank matrix standards.

In one embodiment, a spiked matrix standard may be created by adding a specific amount of an analyte solution containing a specific concentration of the analyte or analytes to the blank matrix. Multiple analyte solutions of varied concentrations may be made, and a consistent volume of each analyte solution may be added to different blank matrix samples to produce a set of spiked matrix standards encompassing a range of analyte loading amounts. In another embodiment, a single solution of analytes may be produced and added to different blank matrix samples in variable volumes to produce a set of spiked matrix standards encompassing a range of analyte loading amounts.

In one embodiment, a spiked matrix standard may be created by adding a specific amount of an analyte solution containing a specific concentration of the analyte or analytes to the blank matrix. Multiple spiked matrix standards of varied concentrations may be made, and subsequently dried to a neat residue on the matrix. In another embodiment, the blank matrix may be a filtered matrix extract that is combined with the analyte or analytes to produce spiked matrix standards.

In one embodiment, spiked matrix standards may be created by adding a specific amount of an internal standard solution of a reference analyte containing a specific concentration of the analyte or analytes to the blank matrix. In various embodiments, the amount of the reference analyte in each spiked matrix standard may range from about 0.001 ng to about 1 gram, or from about 1 ng to about 100 mg, or from about 10 ng to about 100 µg of the reference analyte per spiked matrix standard. In related embodiments, the amount of reference analyte per gram of blank matrix associated with the reference analyte may range from about 0.001 ng to about 500 mg, or from about 1 ng to about 100 mg per gram of blank matrix. Standard curves using the spiked matrix standards of the present disclosure may range from about 0.001 ng/ml to about 1 g/mL, preferably, the spiked matrix standard curve provides an actual (non-extrapolated standard curve) ranging from about 0.1 ng/mL to about 1 mg/mL, when determined using a quantitative analysis as recited herein.

In one embodiment, a specific concentration level of analyte-containing spiked matrix standards is formulated in a colored matrix carrier for use as a color-coding system to indicate each concentration level by color.

In one embodiment, the spiked matrix standards are supplied in blister packaging or another similar packaging system that enables labeling, organization, convenient storage, and dispensing of each spiked and/or blank matrix standard.

In one embodiment, the residual solvent contained within the spiked matrix standard sample is removed via heating, evaporation at atmospheric or reduced pressure, lyophilization, or by subjecting the spiked matrix with a stream of inert gas such as nitrogen or argon. In another embodiment, the residual solvent contained within the spiked matrix standard is not removed.

Another aspect of the present disclosure provides extraction solutions for the use of constituting the spiked matrix standards, blank matrix standards, and samples to be tested.

Another aspect of the present disclosure provides extraction solutions that contains internal standard and/or internal standard surrogates of the analytes used in the spiked matrix standards.

In one embodiment, the matrix for use in the spike matrix standards is a plant-based solid in a dehydrated form. In some embodiments the plant solid is a solid material having a residual moisture content ranging from about 2% to about 0.001%. In various embodiments the dehydrated plant solid is further processed to create a powdered material having an average particle size ranging from about 10 µm to about 1000 µm.

Carriers

In some embodiments the spiked matrix standard is contained in a carrier, also referred to herein, and used interchangeably with the term "matrix carrier". The carrier is merely a convenient receptacle, vessel, or container in which to store the spiked matrix standard. Typically, the carrier is a solid that has an internal volume ranging from about 0.1 mL to about 15 mL and all volumes there between. In related embodiments, the carrier is a hard or solid material that permits storage of the spiked matrix standard or blank matrix. In various embodiments, the carrier may be dissolvable in aqueous, or organic solvents. In some embodiments, the blank matrix is encapsulated in a carrier, such as a capsule. In another embodiment, the blank matrix is a solid food ingredient in granular, powdered or other solid form, such as a corn starch, brownie mix, pulverized cookie crumbles, or a gelatin gummy-based food product in solid/gelatinous form, such as a gummy candy encapsulated in a capsule or other carrier. In some embodiments the carrier is a dissolvable tablet when formulated with the plant or food solid in powdered or granulated form, provides a dissolvable composition when added to the extraction solution. In some embodiments, the carrier and/or blank matrix may include a food product, for example, a candy product, or gelatin product formed into a shape, wherein the carrier comprising the candy or gelatin product may be shaped in the form of a common candy or food product containing the blank matrix and the reference analyte.

In various embodiments, the blank matrix for use in the device, kits and methods of the present disclosure comprises a solid plant extract, corn starch, brownie mix, pulverized cookie crumbles, or a gelatin containing food product. For example, the blank matrix may include a solid plant extract. In examples, where the blank matrix is a solid plant extract, the solid plant extract or material has a moisture content ranging from about 2% to about 0.001%, and may comprise plant tissue selected from at least one plant part, for example, leaves, stems, flowers, roots, rhizomes, or combinations thereof.

In a preferred embodiment, the solid plant extract or material for use as a blank matrix, in the preparation of spiked matrix standards and blank matrix controls may include a solid plant material obtained from: *Cannabis sativa, Cannabis* indinca or *Cannabis ruderalis*.

Other plants that may be used as a blank matrix material may include: solid plant extract/material from the leaves, stems, buds, flowers, shoots, rhizomes, bark, or combinations thereof of a *cannabis* plant (*Cannabis sativa, Cannabis* indinca or *Cannabis ruderalis*) or a similar plant, e.g. Japanese maple, coral plant, okra, cranberry hibiscus, cassava, sweetfern, cleome, texas star hibiscus, kenaf, *Tagetes minuta*, chaste tree, tomato, hops, nettle, blue lotus or liverwort), or a different type of plant, or combinations thereof.

In another embodiment, the blank matrix is an oil, such as olive oil contained within a solid carrier, for example, a gelatin capsule.

In one embodiment, the carrier used consists of various materials including but not limited to gelatin, HPMC, fish gelatin, starch, pullulan, polyvinyl acetate (PVA), or another material that is a suitable matrix carrier. Matrix carriers may be in different sizes or shapes depending on the amount of matrix used and the size of the extraction solution vessel. In one embodiment, the matrix carrier is an empty size 00 gelatin 2-piece capsule with head and body components. In another embodiment, the matrix carrier may be designed to mechanically release the contents held within the carrier upon addition to the ES.

In another embodiment, the matrix carrier may be designed to mechanically release the contents held within the carrier upon addition to the ES vessel.

In another embodiment, the carrier is a glass or plastic vial or tube or related vessel that may be used to reconstitute the spiked matrix standard with the ES.

In one embodiment, the ES is a solution consisting of a single aqueous or organic solvent, such as acetonitrile, acetone, dimethyl sulfoxide (DMSO), methanol, ethanol, butanol, dichloromethane, chloroform, diethyl ether, MTBE, pentanes, hexanes, tetrahydrofuran, or toluene.

In another embodiment, the ES is a solution consisting of a mixture of aqueous or organic solvents, such as acetonitrile, acetone, dimethyl sulfoxide (DMSO), methanol, ethanol, butanol, dichloromethane, chloroform, diethyl ether, MTBE, pentanes, hexanes, tetrahydrofuran, or toluene.

In one embodiment, the ES is an aqueous solution, with or without buffer components, and of acidic, neutral, or basic pH.

In one embodiment, the ES is a solution that is contained within a scalable vessel. In one embodiment, the ES is a 10 mL solution that is contained within a scalable tube that is made of glass or plastic.

In one embodiment, the ES solution may be reconstituted from a neat residue that is contained within a sealable vessel. In one example, it is a neat residue of the internal standard delta-9-THC-d3(item #19332 purchased from Cayman Chemical, Ann Arbor MI) contained within a scalable 100 ml bottle made of glass or plastic and reconstituted with 100 mL of methanol to form the ES.

In one embodiment, the spiked matrix standard is contained within a QUECHER tube, e.g. SampliQ QuEChERS extract tubes (Agilent Technologies, item 5982-5550).

In another embodiment, the ES is a solution that is contained within a QUECHER tube, e.g. SampliQ QUEChERS extract tubes (Agilent Technologies, item 5982-5550).

In one embodiment, the spiked matrix standard is contained within a bead homogenization tube. In some embodiments, a bead homogenization tube is a tube containing spherical particles within a tube, such as a rescalable tube used for liquid extraction and optionally centrifugation. Typically, the beads are spherical beads made of ceramic, glass or metal.

In one embodiment, the ES is a solution that is contained within a bead homogenization tube. Bead-filled homogenizer tubes can range in size from about 0.1 mL, 0.5 mL, to about 50 mL or 100 mL, and all sizes there between. In some embodiments, the bead-filled homogenizer tube is commercially available (See for example, Cat. No. SKU 19-6158, Omni International Kennesaw GA, USA). While any homogenizing technique may be used to assist in the degradation of the carrier and/or the spiked matrix standard and/or the test sample material, mechanical homogenizers, for example: Potter-Elvehjem tissue homogenizers, Dounce glass tissue homogenizers. Tenbroeck glass homogenizers, and BioMasher homogenizers may be successfully employed.

In one embodiment, a spiked matrix standard is added to the ES and mixed and or extracted via mechanical or manual shaking for a given time period.

In one embodiment, a spiked matrix standard is added to the ES and mixed and or extracted via bead homogenization for a given time period.

One aspect of the present disclosure includes a sample preparation step after extraction of the spiked matrix in the ES vessel. The extraction solution may be further processed to remove solid and particulate matter from the solution by a variety of techniques including but not limited to filtration, centrifugation, and decantation.

In one embodiment, the spiked matrix ES or a portion of the spiked matrix ES is transferred to a centrifuge tube, spun for a given time period, and the supernatant transferred to another tube or vial, such as a vial used for mass spectrometry.

In some embodiments, the present disclosure provides methods for determining the concentration of one or more analytes in any number of test samples using the methods of the present disclosure. In one illustrative embodiment, the method comprises the steps: i) providing a device of the present invention wherein the device comprises: a) a plurality of spiked matrix calibration standards with a range of analyte concentrations, b) spiked matrix quality control standards with a range of analyte concentrations, and c) blank matrix standards that are the same or similar physical material as the test sample but devoid of the analytes to be quantified; ii) optionally providing at least one extraction solution (ES) for each spiked matrix calibration standard and test sample; iii) optionally combining each spiked matrix calibration standard, each spiked matrix quality control standard, each blank matrix, and each test sample for analysis to a separate ES vessel; iv) mixing the spiked matrix standards, blank matrix, and samples within the ES; v) filtering, centrifuging, or other preparative work to the ES vessel mixtures before analysis to provide a liquid fraction of the ES vessel mixture of each spiked matrix calibration standard, each spiked matrix quality control standard, each blank matrix, and each test sample; and vi) quantifying the concentrations of the analytes present in the spiked matrix calibration standards, spiked matrix quality control standards, and the test samples.

In some embodiments, the present disclosure provides a method for determining an amount or concentration of a test analyte in a sample. The method can be practiced in several illustrative ways, but the features or steps may include: (i) reconstitution of the spiked matrix standards and the test samples in the ES, (ii) mixing of the ES mixture, (iii) optionally filtration or centrifugation of the ES mixture, and (iv) quantitative analysis of the ES mixture. In step (i), the test sample is prepared by aliquoting an amount of the test sample and transferring into a vessel containing a specific volume of ES. Spiked matrix calibration standards, spiked matrix QC stds, and/or blank matrix standards are added to separate, individual vessels containing a specific volume of ES. In step (ii), the ES tubes containing test sample, spike matrix, or blank matrix are thoroughly mixed by sonication, bead homogenization, hand mixing, or mixed using a vortex mixing apparatus. In optional step (iii), the ES mixture is treated to separate the solids in the ES mixture from the liquid components. For example, the ES mixture can be optionally centrifuged, and/or filtered using any one of a variety of filtration techniques including but not limited to vacuum filtration, use of a syringe microfilter, or use of a 96-well plate filter to obtain one or more clarified standard solutions and one or more clarified test solutions. Alternatively, the particulate matter in the ES mixture may be separated through centrifugation. In step (iv), the liquid fraction of the ES mixture is analyzed using any number of quantitative techniques, including but not limited to GC/MS, LC/MS, ICP/MS, LC-UV/Vis, or LC-fluorescence.

In a further embodiment, a method for performing a qualitative analysis of an analyte, the method comprises: (a) providing one or more test samples to be tested for the presence of the analyte; (b) providing one or more spiked matrix standards; (c) reconstituting the one or more spiked matrix standards and the one or more test samples individually in an extraction solution (ES) to form one or more standard extraction mixtures and one or more test extraction mixtures; (d) separating the liquid solution from the solid material in the one or more standard extraction mixtures and the one or more test extraction mixtures, thereby forming one or more clarified standard solutions and one or more clarified test solutions; and (e) performing a quantitative analysis of each of the one or more clarified standard solutions and each of the clarified one or more test solutions.

In a related embodiment, the methods of the present disclosure provide for accurate quantitative and/or qualitative determination of one or more analytes from one or more test samples. In such examples, the method comprises the steps: i) providing a device of the present disclosure wherein the device comprises a plurality of spiked matrix calibration standards with a range of analyte concentrations, spiked matrix quality control standards with a range of analyte concentrations, and blank matrix standards devoid of the analytes to be quantified; ii) adding at least one extraction solution (ES) for each spiked matrix calibration standard and test sample; iii) mixing the spiked matrix standards, blank matrix, and test samples within the ES; iv) separating any solids from the liquid component in the mixtures before analysis to obtain one or more clarified standard solutions and one or more clarified test solutions; and v) quantifying the concentrations of the analytes present in the spiked matrix calibration standards, spiked matrix quality control standards and test samples, for example, the clarified spiked matrix calibration standards, clarified spiked matrix quality control standards, and the clarified test samples. In various embodiments, step iii) does not require the step of combining each spiked matrix calibration standard, each spiked matrix quality control standard, each blank matrix, and each sample for analysis to a separate ES vessel; rather the rather the spiked matrix calibration standards, spiked matrix quality control standards and test samples are each individually reconstituted in the vessel, and no further treatment is required after reconstitution after admixture with the ES.

In one embodiment, a spiked matrix standard (i.e. a spiked matrix calibration standard or a spiked matrix quality control standard) is added to the ES, and mixed and/or extracted via vortex mixing for a given time period. In one embodiment, the ES is added to the spiked matrix standard within a vessel (i.e. a matrix carrier, such as an ES vessel), such as a vial, tube (e.g. a test tube, or Eppendorf tube and the like) or other vessel, QUECHER tube, or bead-filled homogenizer tube, and mixed and/or extracted and/or sonicated for a given time period.

In some embodiments, the analyte(s) to be quantified in a test sample are cannabinoids, and other natural constituents of various varieties of the *Cannabis* plant such as *Cannabis sativa*, *Cannabis* indica or *Cannabis ruderalis*. These constituents may include but are not limited to the following analytes: delta-9-THC, delta-8-THC, THCA, THCA-A, CBN, CBD, CBDA, CBG, CBC, THCV, CBV, CBDV, CBND, CBE, CBL, CBT, CBCV, CBGV, CBGM, Myrcene, Limonene, Linalool, Caryophyllene, alpha-Pinene, beta-Pinene, alpha-bisabolol, Eucalyptol, trans-Nerolidol, Humelene, delta-3-Carene, Camphene, Borneol, Terpineol, Terpinolene, Phellandrene, Humulene, Pulegon, Sabinene, Valencene, and Geraniol. These substances to be tested and quantified are therefore, also the reference standards used to determine their concentration in test samples.

In some embodiments, the analyte(s) to be quantified in a test sample are synthetic drugs and other non-natural occurring substances. These constituents may include but are not limited to synthetic cannabinoids, cathinones, opioids, and hallucinogens. Exemplary synthetic cannabinoids include 1-naphthalenyl(1-pentyl-1H-indol-3-yl)-methanone (JWH-018), (1-(5-fluoropentyl)-1H-indol-3-yl)(2,2,3,3-tetramethylcyclopropyl)methanone (XLR-11), (S)—N-(1-amino-3-methyl-1-oxobutan-2-yl)-1-pentyl-1H-indazole-3-carboxamide (AB-PINACA), and N-[1-(aminocarbonyl)-2,2-dimethylpropyl]-1-(cyclohexylmethyl)-1H-indazole-3-carboxamide (MAB-CHMINACA), as well as analogs of these substances. Exemplary synthetic cathinones include 1-(1,3-benzodioxol-5-yl)-2-(1-pyrrolidinyl)-1-pentanone (MDPV), α-Pyrrolidinovalerophenone (α-PVP), and 2-(butylamino)-1-phenyl-1-hexanone (α-Butylaminohexanophenone) as well as analogs of these substances. Exemplary synthetic opioids include furanyl fentanyl, trans-3,4-dichloro-N-[2-(dimethylamino)cyclohexyl]-N-methyl-benzamide (U-47700), and 4-chloro-N-[1-[2-(4-nitrophenyl)ethyl]-2-piperidinylidene]-benzenesulfonamide (W-18) as well as analogs of these substances. Exemplary synthetic hallucinogens include 4-iodo-2,5-dimethoxy-N-[(2-methoxyphenyl)methyl]-benzeneethanamine (25I-NBOMe), α-methyl-5-benzofuranethanamine (5-APB), and 4-chloro-2,5-dimethoxy-benzeneethanamine (2C—C) as well as analogs of these substances.

In some embodiments, the analyte(s) to be quantified in a test sample may include pesticides, heavy metals, natural products, synthetic products, for example, medicaments, synthetic drugs, narcotics, and other non-endogenous substances that may be found to occur on various foods, plants and products, for example, varieties of the *Cannabis* and hemp plant. These constituents may include but are not limited to the following pesticide analytes and their internal standards and/or internal standard surrogates: Abamectin, Acephate, Acetamiprid, Acequinocyl, Aldicarb, Allethrin, Azadiractin, Azoxystrobin, Benzovindiflupyr, Bifenazate, Bifenthrin, Boscalind, Buprofezin, Carbaryl, Carbofuran, Chlorantraniliprole, Chlorphenapyr, Chlorpyrifos, Clofentezine, Clothianidin, Coumaphos, Cyantraniliprole, Cyfluthrin, Cypermethrin, Cyprodinil, Daminozide, Deltamethrin, Diazinon, Dichlorvos, Dimethoate, Dimethomorph, Dinotefuran, Dodemorph, Endosulfan-alpha, Endosulfan-beta, Endosulfan sulfate, Ethoprophos, Etofenprox, Etoxazole, Etridiazol, Fenoxycarb, Fenpyroximate, Fensulfothion, Fenthion, Fenvalerate, Fipronil, Flonicamid, Fludioxonil, Fluopyram, Hexythiazox, Imazalil, Imidacloprid, Iprodione, Kinoprene, Kresoxim-methyl, Malathion, Metalaxyl, Methiocarb, Methomyl, Methoprene, Methyl parathion, Mevinphos, MGK-264, Myclobutanil, Naled, Novaluron, Oxamyl, Paclobutrazol, Permethrin, Phenothrin, Phosmet, Piperonyl butoxide, Pirimicarb, Prallethrin, Propiconazole, Propoxur, Pyraclostrobin, Pyrithrins, Pyradaben, Quintozene, Resmethrin, Spinetoram, Spinosad, Spirodiclofen, Spiromesifen, Spirotetramat, Spiroxamine, Tebuconazole, Tebufenozide, Teflubenzuron, tetrachlovinphos, Tetramethrin, Thiscloprid, Thiamethoxam, Thiophanate-methyl, Trifloxystrobin. These constituents may include but are not limited to the following heavy metals: Mercury, Lead, Arsenic, and Cadmium.

In some embodiments, the analyte(s) to be quantified in a test sample are drug formulations of unknown content including but not limited to counterfeit tablets and capsules, generic medicines, and herbal products. These formulations may contain, but are not limited to excipients, binders, and antiadherents, such as magnesium stearate, sodium bicarbonate, sodium carbonate, sucrose, lactose, starches, cellulose, hydroxypropyl cellulose, xylitol, sorbitol, mannitol, polyvinylpyrrolidone, and polyethylene glycol. In some embodiments, the analyte(s) to be quantified in a test sample may include natural and synthetic constituents of various food products.

In some embodiments, the analyte(s) to be quantified in a test sample may include drug formulations of unknown content including but not limited to counterfeit tablets and capsules, generic medicines, and herbal supplements.

Use of the spiked matrix standards in testing kits and devices

The devices of the present disclosure simplify the task of preparing standards and test samples for quantitative analysis. The device or kit of the present disclosure may be precisely manufactured to yield consistent results and to reduce the error that can accompany sample preparation, for example, liquid transfer mistakes when aliquoting a solution using a robotic liquid handler or hand-pipette to an incorrect tube or well-plate position, the transfer of the wrong amount of liquid, the transfer of an incorrect analyte, omission of a required analyte, and calculations errors of the solution concentrations.

As used herein, a "set of spiked matrix standards" may comprise one or more spiked matrix standards which may include one spiked matrix calibration standard, one spiked matrix calibration standard and one spiked matrix quality control standard, one spiked matrix calibration standard and two or more spiked matrix quality control standards, two or more spiked matrix calibration standards, or two or more spiked matrix calibration standards and one or more spiked matrix quality control standards.

The devices and kits of the present disclosure incorporate the analytes of interest directly onto or within a blank matrix. The blank matrix is a substance that is chemically and physically similar or compatible with a tested sample matrix, or in other words the material or composition of matter that is associated with the analyte of interest. For example, when measuring the presence and/or amount of THC analyte in a test sample (e.g. in a *cannabis* plant), the blank matrix may include plant material, for example, leaves, stems, buds, flowers, shoots, rhizomes, bark, or combinations thereof of the same plant (i.e. *cannabis* plant (*Cannabis* indica and *Cannabis* sativa) or a similar plant, e.g. Japanese maple, coral plant, okra, cranberry hibiscus, cassava, sweetfern, cleome, texas star hibiscus, kenaf, *Tagetes minuta*, chaste tree, tomato, hops, nettle, blue lotus or liverwort), or a different type of plant. The blank matrix and spiked matrix standards are processed in the same manner according to the type of sample that is to be tested and the methodology that is utilized by the individuals performing the sample testing. Since the spiked matrix standards are processed in the same manner as the sample to be tested (test sample), the devices and kits described herein provide improved precision in quantitative results. In another illustrative example, if the analyte in the test sample is delta-9-THC in a gummy candy test sample, the spiked matrix standards would also be formulated in a similar gummy material.

Qualitative Analyses

For the measurement of the one or more analytes in the test sample and in the spiked matrix standards, a quantitative analytical method, such as chromatography, spectroscopy, and mass spectrometry, may be employed, while mass spectrometry is particularly preferred. The chromatography may comprise GC, LC, HPLC, and HPLC; spectroscopy may comprise UV/Vis, Diode Array, IR, and NMR; and mass spectrometry may comprise ESI-QqQ, ESI-QqTOF, MALDI-QqQ. MALDI-QqTOF, and MALDI-TOF-TOF. Preferred is the use of FIA- and HPLC-tandem mass spectrometry. These analytical methods are generally known to the skilled person.

Analysis of the analyte can be performed by any suitable method, such methods are well known in the art, for example gas chromatography (GC), quantitative mass spectrometry tandem mass spectroscopy (MS/MS), liquid chromatography-electrospray tandem mass spectrometry (LC-MS/MS), or liquid chromatography-electrospray time-of-flight mass spectrometry. In other embodiments, analysis of the extracted test sample can be performed by any quantitative analytical method, for example, a mass spectrometric method, an electrophoretic method, NMR, a chromatographic method, or a combination thereof. In a further embodiment, the mass spectrometric method is LC-MS and LC-MS/MS. In some embodiments, the LC-MS/MS can be performed using LC-Orbitrap, LC-FTMS, LC-LTQ, MALDI-MS including but not limited to MALDI-TOF, MALDI-TOF/TOF, MALDI-qTOF, and MALDI-QIT. Preferably, the mass spectrometric method is a quantitative MALDI-MS or LC-MS using optimized conditions. In still another embodiment, the electrophoretic method is CE-LIF. In yet another embodiment, methods such as capillary gel electrophoresis or capillary zone electrophoresis can be used with the inventive methods.

Kits

Figure 3:
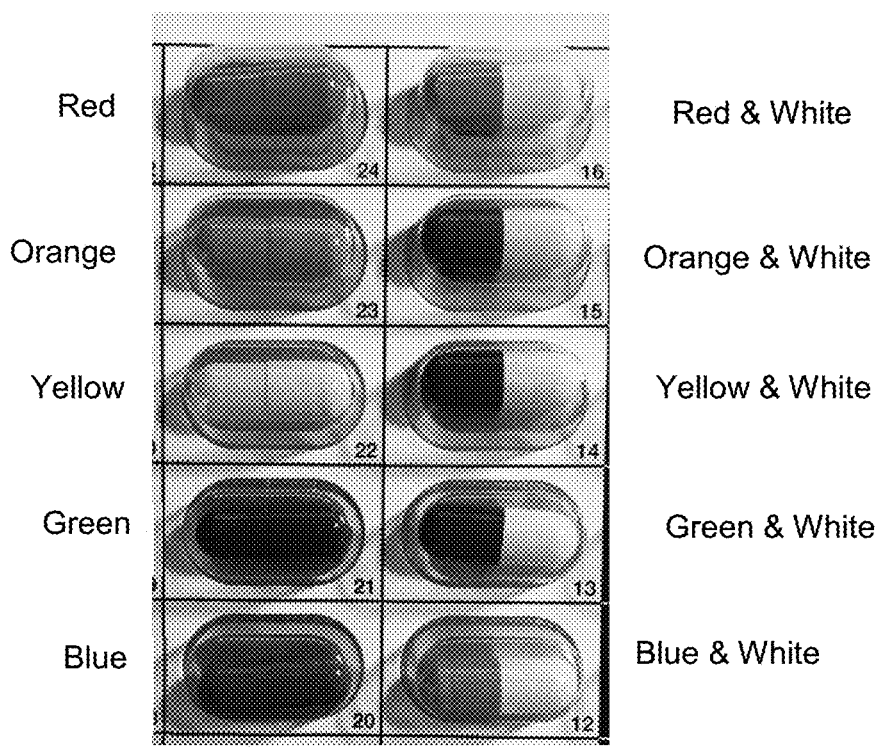
FIG. 3 illustrates a set of five color coded spiked matrix calibrator standards and 5 spiked quality control standards.
Figure 4:
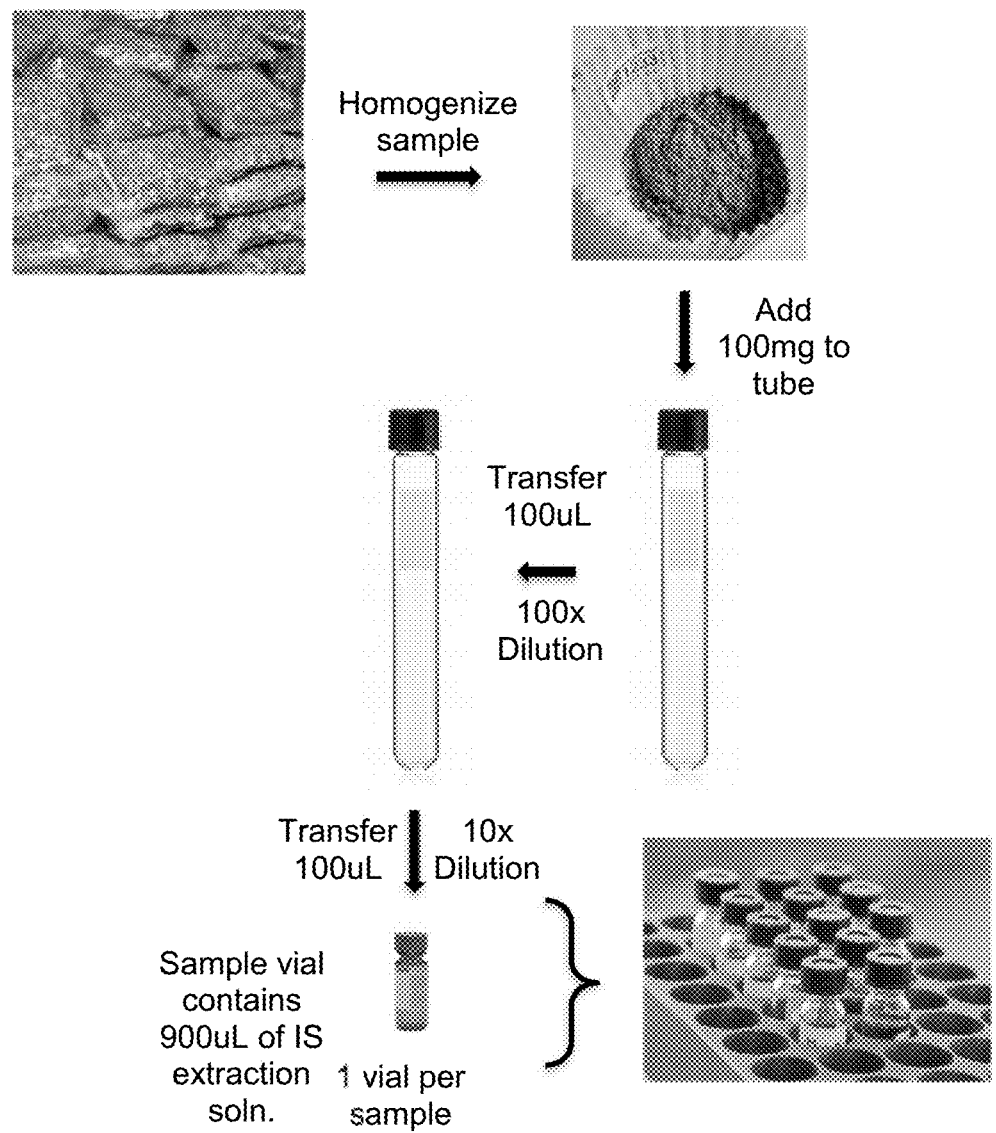
FIG. 4 illustrates the workflow of sample analysis of a bulk sample of Cannabis or hemp plant material with the incorporation of a second ES vessel for use as a dilution step.
Figure 5:
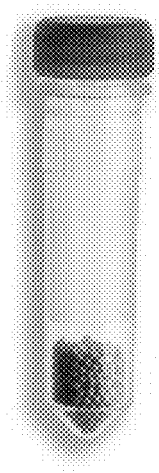
FIG. 5 depicts a bead homogenizer tube.
Figure 6:
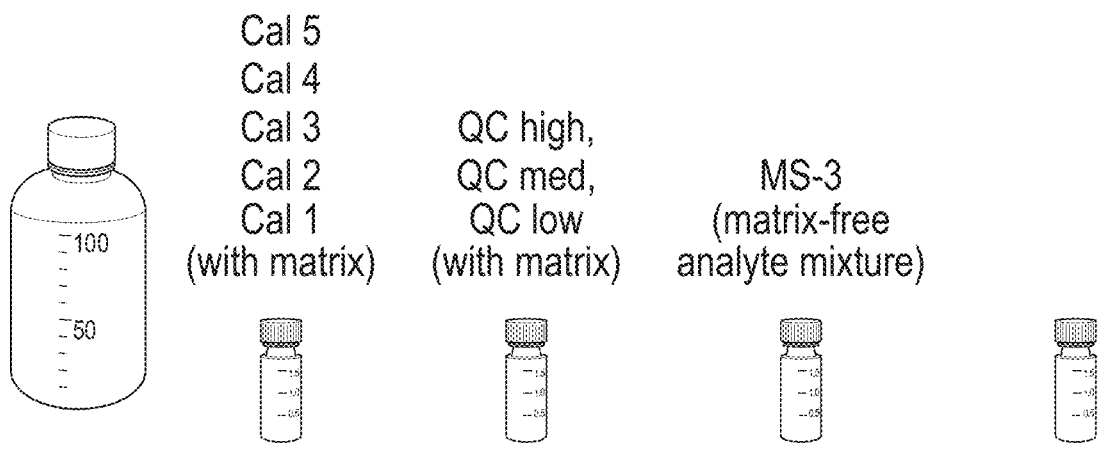
FIG. 6 depicts the workflow of a set of spiked matrix calibrator, quality control, matrix-free, and blank standards formulated in vials.

In various embodiments, the components described herein for the quantitative and/or qualitative analysis of one or more analytes can be performed using a kit or device. For example, spiked matrix standards, and optionally, their respective carriers may be packaged in a kit. As shown in FIG. 3, the spiked matrix standards may be packaged in a blister package containing capsule carriers, each carrier color coded to contain a specific concentration of reference analyte or types of reference analyte. As used herein, kits may be used to quantify one or more analytes in a test sample. One embodiment of a kit of the present disclosure includes a kit comprising: an assay substrate, for example a multi-well plate, one or more vials or one or more tubes for creating the spiked matrix standards, test samples, blanks etc, a set of spiked matrix standards as shown in FIG. 3, and optionally, a blank matrix, either packaged in a separate container or in a carrier similar to the carriers used for the spiked matrix standards, one or more solvents, extraction devices, for example a homogenizer, one or more diluents and a detailed written description of the specifications of the device and instructions for using the device to perform the chemical analysis and quantification of one or more analytes.

In various embodiments of the kits of the disclosure, the kit may further comprise standard operating procedures for measuring specific analytes in plant material, food products, human urine or blood wherein the procedures are customized to meet specific end user validation requirements.

EXAMPLES

Example 1a. Measurement of Delta-9-Tetrahydrocannabinol containing spiked solid plant matrix calibration standards.

A spiked matrix standard was manufactured by adding THC to a blank plant-based matrix in a size 00 capsule purchased from Capsuline (Dania Beach, FL). Nettle root powder, purchased from Black Seed Herb Inc. (Liberty, NY) lot #NIGNETETRP-1703V058516 was used as the blank plant matrix. A THC (1 mg/mL) certified reference standard was purchased from Cayman Chemical (Ann Arbor, MI). The relative response by MS analysis between a THC-spiked acetonitrile solution (10 mL) with blank matrix was compared to that of a spiked matrix standard of equivalent concentration, reformulated in 10 mL of acetonitrile.

Experimental Methods

The spiked matrix standard was built by spiking 300 mg of blank matrix held within a size 00 gelatin capsule. A 1 mg/5 mL calibration solution was made by adding the THC certified reference material to a 5 mL volumetric flask and diluting to 5 mL with methanol. The spiked matrix standard was made by adding 100 uL of the calibrator solution to a nettle-filled capsule.

Component Table

TABLE 1

An exemplary reference analyte commercially available for use in preparing one or more spiked matrix standards.

| Comp # | Group | Parent CRM | Conc. (mg/ml) | Vendor | Item # | Lot # |
|---|---|---|---|---|---|---|
| 1 | 1 | Delta-9-THC | 1 | Cayman | ISO60157 | 543186 |
| | | | | | THC | |
| loading (µg/tube): | | | | 20.0000 | | |
| Final conc. In ES (ng/mL): | | | | 2000.000 | | |

Reconstitution procedure:

The spiked matrix standard was stored overnight at −80C in a labeled 15 mL conical tube. To reconstitute, the capsule was crushed with a wooden pestle (while cold) and then allowed to warm to room temperature. 10 mL of extraction solution was then added to the tube and vortexed for five seconds, then vortexed again for 5×10 second intervals.

A second tube was prepared by spiking a 10 mL acetonitrile solution with 100 uL of the THC calibration solution along with 300 mg of blank nettle matrix. The mixture was vortexed for five seconds, then vortexed again for 5×10 second intervals.

Sample preparation 0.5 mL of each solution was removed using a disposable 1 ml syringe and then transferred to a 96 well plate by passing through a 0.45 um 13 mm PTFE disc filter purchased from Simsii (Port Irvine, CA). Solutions were delivered to a 96-well plate and the solutions were analyzed by LC-mass-spectrometry (LC-MS).

Results

TABLE 2

Experimental results of THC spiked matrix standard

| Group | ES | Parent CRM | Prep | Extraction Conditions | Conc (ng\mL) | Response | Relative Recovery (%) |
|---|---|---|---|---|---|---|---|
| 1 | ACN | Delta-9-THC | THC spiked ES. + loose matrix | Vortex 5 sec. + 5 × 10 sec. | 2000 | 3457 | — |
| 2 | ACN | Delta-9-THC | THC QuantCap. + ES | Vortex 5 sec. + 5 × 10 sec. | 2000 | 3439 | 99.5 |

Example 1b. Measurement of Delta-9-Tetrahydrocannabinol Containing Spiked Solid Plant Matrix Calibration Standards Reconstituted with Methanol.

Two sets of spiked matrix standard vials were manufactured by adding THC (in methanol) to 2 mL mass spectrometry vials purchased from Alwsci Technologies (Hangzhou City, China). One set of vials contained nettle root extract and one set of vials did not contain any matrix material. Nettle root powder, purchased from Black Seed Herb Inc.

(Liberty, NY), lot #NIGNETETRP-1703V058516 was used as the blank plant matrix and delivered in solution from a prefiltered nettle extract from a 100 mg/mL slurry. Both set of vials were dried to a neat residue at reduced pressure in a vacuum chamber and then reconstituted with methanol. The relative response by LCMS analysis between vials with and without formulation on matrix were compared. The relative response by LCMS analysis between the vials and a set of freshly made calibrator solutions was also compared to the reconstituted vials.

Experimental Methods

Four spiked matrix standards (Cal 1, Cal 2, Cal 3, and Cal 4) were built by adding a 1 mg/mL THC solution (ISO60157 purchased from Cayman Chemical) in methanol to give 200, 1000, 2000, and 5000 ng/vial, respectively. Three sets of vials were produced in duplicate: (1) Calibrators vials from freshly prepared solutions in methanol (no matrix, 1 mL of calibrator solution per vial), (2) Calibrators vials that were prepared without matrix by reconstituting from a dry residue with 1 mL of methanol, and (3) Calibrators vials that were prepared with matrix by reconstituting from a dry residue with 1 mL of methanol. Nettle root powder, purchased from Black Seed Herb Inc. (Liberty, NY) lot #NIGNETETRP-1703V058516 was used as the blank plant matrix. All vials that were dried to a neat residue were created by placing under reduced pressure, sealing with screw caps, then storing overnight at −20 degrees Celsius. These vials were reconstituted with 1 mL of methanol per vial, vortexed for five seconds, then sonicated for two minutes. After reconstitution, each set of vials were evaluated by LCMS.

Results

Example 2. Measurement of Delta-9-Tetrahydrocannabinol in a Hemp Sample and Monitoring Conversion of THCA-A to THC Using Ready-to-Extract Spiked Matrix Standards in Vials Using GCMS A set of spiked matrix standards were manufactured by adding THC to a blank plant-based matrix in 2 mL mass spectrometry vials purchased from Alwsci Technologies (Hangzhou City, China). Multicolored vial caps purchased from Agilent Technologies were used to color code the different concentrations levels of the standards curve. Nettle root powder, purchased from Black Seed Herb Inc. (Liberty, NY), lot #NIGNETETRP-1703V058516 was used as the blank plant matrix. THC (1 mg/mL) and THCA-A certified reference standards were purchased from Cayman Chemical (Ann Arbor, MI). The spiked matrix vials were made by adding a proportional quantity of the representative matrix per mL solvent as the hemp sample being tested. In this example 25 mg was added to each calibrator, QC, and blank vial as a proportional amount to the unknown sample to be tested: 100 mg hemp extracted with 2 mL of extraction solution. Varied concentrations of THC solutions were added to each calibrator and QC vial and then dried to a neat residue at reduced pressure in a vacuum chamber. In the same manner, THCA-A standards were prepared to evaluate the conversion of THCA-A to THC in the sample analysis to ensure accuracy in reporting total THC content. Total THC content is calculated by adding the THC to the THCA-A content×0.877. A ready to reconstitute internal standard extraction solution bottle was made by adding 1 mL of a 5

TABLE 3

Experimental results of THC spiked matrix standard reconstituted with methanol from a dried residue.

| | Control Cal solution | | | Set a: reconstituted, no matrix | | | Set b: reconstituted, with matrix | | |
|---|---|---|---|---|---|---|---|---|---|
| | 1 | 2 | Ave | 1 | 2 | Ave | 1 | 2 | Ave |
| Cal 1 | 10247 | 10996 | 10621.5 | 10454 | 10548 | 10501 | 11129 | 11394 | 11261.5 |
| Cal 2 | 56949 | 58497 | 57723 | 54832 | 55486 | 55159 | 58495 | 59259 | 58877 |
| Cal 3 | 109903 | 117025 | 113464 | 105993 | 107845 | 106919 | 115850 | 116448 | 116149 |
| Cal 4 | 261044 | 274856 | 267950 | 253134 | 262379 | 257756.5 | 273090 | 271921 | 272505.5 |

| a/control (ave) | a/b (ave) | b/control (ave) | b/a (ave) |
|---|---|---|---|
| 98.87% | 93.25% | 106.03% | 107.24% |
| 95.56% | 93.69% | 102.00% | 106.74% |
| 94.23% | 92.05% | 102.37% | 108.63% |
| 96.20% | 94.59% | 101.70% | 105.72% |
| 96.21% | 93.39% | 103.02% | 107.08% |

Table 3 summarizes the relative difference in MS area count of a standard curve of THC from a freshly prepared solution (control) to those that were reconstituted with methanol from a dry residue, with or without the presence of a representative matrix. The calibrator vials that were reconstituted without matrix had an average relative response of 96% relative to the calibrator controls. The calibrator vials that were reconstituted with matrix had an average relative response of 103% relative to the calibrator controls. An average difference in area of 7.1% was observed for the standards Cal 1, 2, 3, and 4 that were formulated with matrix relative to the to the standards that were formulated without matrix. The difference in relative area that was observed highlights the importance of including matrix in quantitative analysis, especially in instances that no internal standard is used to correct for the difference.

mg/mL tribenzylamine solution to a 100 mL plastic bottled with cap. Tribenzylamine was purchased from MilliporeSigma (St. Louis, MO). The internal standard surrogate was evaporated under reduced pressure in a vacuum chamber.

Experimental Methods

The protocol for using this kit is as follows:

1) Reconstitute the internal standard extraction solution by adding 100 mL of blank extraction solvent (MeOH) to the neat residue in the bottle. Mix thoroughly: place on shaker for 15 min.

2) Reconstitute each Cal, QC, MS-1, and acid vial with 500 uL of the internal standards extraction solution (ISex). Thoroughly mix each of the solutions: vortex 3×10 sec, sonicate two minutes.

3) Extract each unknown *Cannabis* sample by combining sample in 2 mL of ISex.
   Sample extraction is to be done according to the method established by the testing laboratory (i.e. vortex, sonication)
   Subject THCA-A samples (post-reconstitution in the extraction solvent) to the same conditions to that of the *Cannabis* samples (i.e. sonicate for the same amount of time)
4) Filter each sample through cotton or through a disc filter into a mass spec vial, or by using GVS Separa® filter vial.
5) Analyze samples
Component Table Example 3. Measurement of Delta-9-Tetrahydrocannabinol in a hemp sample using ready-to-extract spiked matrix standards in vials using GCMS.

A set of spiked matrix standards were manufactured by adding THC to a blank plant-based matrix in 2 mL mass spectrometry vials purchased from Alwsci Technologies (Hangzhou City, China). Multicolored vial caps purchased from Agilent Technologies (Santa Clara, CA) were used to color code the different concentrations levels of the standards curve. Nettle root powder, purchased from Black Seed Herb Inc. (Liberty, NY), lot #NIGNETETRP-1703V058516 was used as the blank plant matrix. THC (item #ISO60157; 1 mg/mL) was purchased from Cayman Chemical (Ann Arbor MI). The spiked matrix vials were made by adding a

TABLE 4

Commercially available reference standards used in preparing the spiked matrix standards.

| Comp # | Group | Parent CRM | Conc. | Vendor | Item# | Lot # |
|---|---|---|---|---|---|---|
| 1 | 1 | Delta-9-THC | 1 | Cayman | ISO60157 | 543186 |
| 2 | 1 | THCA-A | 1 | Cayman | ISO60175 | 0558070 |

| Comp # | Group | Internal Standard CRM (surrogate) | Conc. | Vendor | Item# | Lot # |
|---|---|---|---|---|---|---|
| 1 | 1 | Tribenzylamine (surrogate) | 1 | MilliporeSigma | 90660 | WN3C8413V |

TABLE 5

Concentration tables.

| Samples | | | | | | Extraction Solution | IS |
|---|---|---|---|---|---|---|---|
| sample size (mg): | 100 | | | | | Loading (ug/bottle): | 5000.000 |
| sample reconstitution volume (mL): | 2 | | | | | IS extraction solution (mL): | 100 |
| testing range (% THC by weight): | 0.10% | 0.20% | 0.30% | 0.60% | 1.00% | Final conc. Of matrix spike (ug/mL): | 50.000 |
| concentration table (µg/mL): | 50.0 | 100.0 | 150.0 | 300.0 | 500.0 | | |

| Std Curve | Cal 1 | Cal 2 | Cal 3 | Cal 4 | Cal 5 |
|---|---|---|---|---|---|
| Loading (µg/vial): | 25.0 | 50.0 | 75.0 | 150.0 | 250.0 |
| Matrix quantity (mg): | 25 | 25 | 25 | 25 | 25 |
| Cal vial reconstruction (µL/vial): | 500 | 500 | 500 | 500 | 500 |
| Final conc. Of matrix spike (µg/mL): | 50.0 | 100.0 | 150.0 | 300.0 | 500.0 |

| $2^{nd}$ source QC | QC-L | QC-M | QC-H |
|---|---|---|---|
| Loading (µg/vial): | 50.0 | 75.0 | 150.0 |
| Matrix quantity (mg): | 25 | 25 | 25 |
| QC vial reconstitution (µL/vial): | 500 | 500 | 500 |
| Final conc. Of matrix spike (µg/mL): | 100.0 | 150.0 | 300.0 |

| ES - acid (on matrix) | ES - acid | Post-deconjunction THC levels: | |
|---|---|---|---|
| Loading (µg/vial): | 85.493 | }----> 75.0000 | MW of THCA-A: 358.5 |
| Matrix quantity (mg): | 25 | 25 | MW of THC: 314.5 |
| QC vial reconstitution (µL/vial): | 500 | 500 | |
| Final conc. Of matrix spike (µg/mL): | 170.986 | }----> 150 | | pre-filtered aliquot of the representative matrix extracted from methanol. In this example, a 100 mg/mL slurry of the representative matrix was sonicated for 15 minutes, shaken on a mechanical shaker table for 15 minutes, then filtered. An aliquot of the resulting solution was added to each calibrator, QC, and blank vial that was proportional to the unknown sample to be tested: 100 mg hemp extracted with 2 mL of extraction solution. Varied concentrations of THC solutions were added to each calibrator and QC vial, and then dried to a neat residue at reduced pressure in a vacuum chamber. A ready to reconstitute internal standard extraction solution bottle was made by adding 1 mL of a 5 mg/mL tribenzylamine solution to a 100 mL plastic bottled with cap, then evaporating under reduced pressure in a vacuum chamber.

Experimental Methods

The protocol for using this kit is as follows:
1) Reconstitute the internal standard extraction solution by adding 100 mL of blank extraction solvent (MeOH) to the neat residue in the bottle. Mix thoroughly: place on shaker for 15 min.
2) Reconstitute each Cal, QC. MS-3, and acid vial with 750 uL of the internal standards extraction solution (ISex). Thoroughly mix each of the solutions: vortex 3×10 sec, sonicate two minutes.
3) Extract each unknown *Cannabis* sample by combining sample in 2 mL of ISex.
   a. Sample extraction is to be done according to the method established by the testing laboratory (i.e. vortex, sonication)
   b. Filter unknown samples
4) Analyze samples Component Table

TABLE 6

Commercially available reference standards used in preparing the spiked matrix standards.

| Comp # | Group | Parent CRM | Conc. | Vendor | Item# | Lot # |
|---|---|---|---|---|---|---|
| 1 | 1 | Delta-9-THC | 1 | Cayman | ISO60157 | 543186 |

| Comp # | Group | Internal Standard CRM (surrogate) | Conc. | Vendor | Item# | Lot # |
|---|---|---|---|---|---|---|
| 1 | 1 | Tribenzylamine (surrogate) | 1 | Aldrich | 90660 | WN3C8413V |

TABLE 7

Concentration tables.

| Samples | | | | | | Extraction Solution | IS |
|---|---|---|---|---|---|---|---|
| sample size (mg): | 100 | | | | | Loading (µg/bottle): | 5000.000 |
| sample reconstitution volume (mL): | 2 | | | | | IS extraction solution (mL): | 100 |
| testing range (% THC by weight): | 0.10% | 0.20% | 0.30% | 0.60% | 1.00% | Final conc. Of matrix spike (µg/mL): | 50.000 |
| concentration table (µg/mL): | 50.0 | 100.0 | 150.0 | 300.0 | 500.0 | | |

| Std Curve | Cal 1 | Cal 2 | Cal 3 | Cal 4 | Cal 5 |
|---|---|---|---|---|---|
| Loading (µg/vial): | 37.5 | 75.0 | 112.5 | 225.0 | 375.0 |
| Matrix quantity (mg): | 37.5 | 37.5 | 37.5 | 37.5 | 37.5 |
| Cal vial reconstitution (µL/vial): | 750 | 750 | 750 | 750 | 750 |
| Final conc. Of matrix spike (µg/mL): | 50.0 | 100.0 | 150.0 | 300.0 | 500.0 |

| $2^{nd}$ source QC | | QC-L | QC-M | QC-H | |
|---|---|---|---|---|---|
| Loading (µg/vial): | | 75.0 | 112.5 | 225.0 | |
| Matrix quantity (mg): | | 37.5 | 37.5 | 37.5 | |
| QC vial reconstitution (µL/vial): | | 750 | 750 | 750 | |
| Final conc. Of matrix spike (µg/mL): | | 100.0 | 150.0 | 300.0 | |

Sample details:

A commercially available hemp certified reference standard was purchased from Absolute Standards (Hamden, CT); item number #54999B, lot #012020. Three samples were weighed into 15 mL plastic conical tubes. Sample 1 weight=100.8 mg. Sample 2 weight=102.4 mg. Sample 3 weight=101.7 mg.

TABLE 8

Experimental results

| Hemp CRM Sample | Sample Weight (mg) | Total % THC Content Measured Using Kit of present disclosure (weight corrected) | Reported total % THC of Certified Hemp Standard | Kit value (%) relative to Certified Value |
| --- | --- | --- | --- | --- |
| 1 | 100.8 | 0.2668 | 0.2438 | 109.43% |
| 2 | 102.4 | 0.2334 | 0.2438 | 95.73% |
| 3 | 101.7 | 0.2385 | 0.2438 | 97.83% |
| average | | 0.2462 | 0.2438 | 101.00% |

What is claimed is:

1. A method for determining the concentration of one or more analytes in a test sample, the method comprising the steps:
   i) providing at least one test sample and a plurality of spiked matrix calibration standards with a range of analyte concentrations, wherein the analyte in the plurality of spiked matrix calibration standard is identical to the one or more analytes to be quantified in the at least one test sample, and wherein the each of the plurality of spiked matrix calibration standards comprises the one or more analytes and an extract isolated from an admixture comprising a solid blank matrix and an extraction solution wherein the at least one test sample comprises the extraction solution, and;
   ii) quantifying the concentrations of the one or more analytes present in the plurality of spiked matrix calibration standards, and the at least one test samples.

2. The method of claim 1, wherein the one or more analytes to be quantified comprises delta-9-THC, delta-8-THC, THCA, THCA-A, CBN, CBD, CBDA, CBG, CBC, THCV, CBV, CBDV, CBND, CBE, CBL, CBT, CBCV, CBGV, CBGM, Myrcene, Limonene, Linalool, Caryophyllene, alpha-Pinene, beta-Pinene, alpha-bisabolol, Eucalyptol, trans-Nerolidol, Humelene, delta-3-Carene, Camphene, Borneol, Terpineol, Terpinolene, Phellandrene, Humulene, Pulegon, Sabinene, Valencene, Geraniol, cathiones, 1-naphthalenyl(1-pentyl-1H-indol-3-yl)-methanone (JWH-018), (1-(5-fluoropentyl)-1H-indol-3-yl)(2,2,3,3-tetramethylcyclopropyl)methanone (XLR-11), (S)—N-(1-amino-3-methyl-1-oxobutan-2-yl)-1-pentyl-1H-indazole-3-carboxamide (AB-PINACA), and N-[1-(aminocarbonyl)-2,2-dimethylpropyl]-1-(cyclohexylmethyl)-1H-indazole-3-carboxamide (MAB-CHMINACA), analogs of these substances, 1-(1,3-benzodioxol-5-yl)-2-(1-pyrrolidinyl)-1-pentanone (MDPV), α-Pyrrolidinovalerophenone (α-PVP), and 2-(butylamino)-1-phenyl-1-hexanone (α-Butylaminohexanophenone), analogs thereof, furanyl fentanyl, trans-3,4-dichloro-N-[2-(dimethylamino)cyclohexyl]-N-methyl-benzamide (U-47700), and 4-chloro-N-[1-[2-(4-nitrophenyl)ethyl]-2-piperidinylidene]-benzenesulfonamide (W-18), analogs thereof, 4-iodo-2,5-dimethoxy-N-[(2-methoxyphenyl)methyl]-benzeneethanamine (25I—NBOMe), α-methyl-5-benzofuranethanamine (5-APB), and 4-chloro-2,5-dimethoxy-benzenethanamine (2C—C), analogs thereof, heavy metals, natural products, medicaments, synthetic drugs, narcotics, Abamectin, Acephate, Acetamiprid, Acequinocyl, Aldicarb, Allethrin, Azadiractin, Azoxystrobin, Benzovindiflupyr, Bifenazate, Bifenthrin, Boscalind, Buprofezin, Carbaryl, Carbofuran, Chlorantraniliprole, Chlorphenapyr, Chlorpyrifos, Clofentezine, Clothianidin, Coumaphos, Cyantraniliprole, Cyfluthrin, Cypermethrin, Cyprodinil, Daminozide, Deltamethrin, Diazinon, Dichlorvos, Dimethoate, Dimethomorph, Dinotefuran, Dodemorph, Endosulfan-alpha, Endosulfan-beta, Endosulfan sulfate, Ethoprophos, Etofenprox, Etoxazole, Etridiazol, Fenoxycarb, Fenpyroximate, Fensulfothion, Fenthion, Fenvalerate, Fipronil, Flonicamid, Fludioxonil, Fluopyram, Hexythiazox, Imazalil, Imidacloprid, Iprodione, Kinoprene, Kresoxim-methyl, Malathion, Metalaxyl, Methiocarb, Methomyl, Methoprene, Methyl parathion, Mevinphos, MGK-264, Myclobutanil, Naled, Novaluron, Oxamyl, Paclobutrazol, Permethrin, Phenothrin, Phosmet, Piperonyl butoxide, Pirimicarb, Prallethrin, Propiconazole, Propoxur, Pyraclostrobin, Pyrithrins, Pyradaben, Quintozene, Resmethrin, Spinetoram, Spinosad, Spirodiclofen, Spiromesifen, Spirotetramat, Spiroxamine, Tebuconazole, Tebufenozide, Teflubenzuron, tetrachlovinphos, Tetramethrin, Thiscloprid, Thiamethoxam, Thiophanate-methyl, Trifloxystrobin, Mercury, Lead, Arsenic, and Cadmium.

3. The method according to claim 1, wherein the solid blank matrix comprises a solid material selected from the group consisting of: a plant extract, corn starch, brownie mix, pulverized cookie crumbles, a gelatin containing food product, and combinations thereof.

4. The method according to claim 3, wherein the blank matrix comprises a solid plant extract.

5. The method according to claim 4, wherein the solid plant extract comprises a plant material that has a moisture content ranging from 2% to 0.001%, and comprises plant tissue selected from at least one plant part comprising leaves, stems, flowers, roots, or combinations thereof.

6. The method according to claim 1, wherein the one or more analytes in the at least one test samples to be quantified is at least one analyte that is found associated with the plants: *Cannabis sativa, Cannabis* indica or *Cannabis ruderalis*.

* * * * *